(12) United States Patent
Cox

(10) Patent No.: US 6,265,207 B1
(45) Date of Patent: Jul. 24, 2001

(54) STRENGTH LOSS RESISTANT METHODS FOR IMPROVING THE SOFTENING OF COTTON TOWELING AND RELATED FABRICS

(75) Inventor: Thomas C. Cox, Rock Hill, SC (US)

(73) Assignee: Genencor International, Inc., Palo Alto, CA (US)

( * ) Notice: Subject to any disclaimer, the term of this patent is extended or adjusted under 35 U.S.C. 154(b) by 0 days.

(21) Appl. No.: 09/420,416

(22) Filed: Oct. 19, 1999

Related U.S. Application Data

(63) Continuation of application No. 08/117,648, filed on Sep. 8, 1993, now Pat. No. 6,156,562, which is a continuation of application No. 07/810,962, filed on Dec. 20, 1991, now abandoned.

(51) Int. Cl.⁷ .................................................. D06M 16/00

(52) U.S. Cl. ................ 435/263; 435/209; 26/1; 28/100; 8/116.1

(58) Field of Search ..................................... 435/209, 263; 26/1; 28/100; 8/116.1

(56) References Cited

U.S. PATENT DOCUMENTS

| | | |
|---|---|---|
| 3,650,673 | 3/1972 | Ehner . |
| 4,435,307 | 3/1984 | Barbesgaard et al. . |
| 4,479,881 | 10/1984 | Tai . |
| 4,489,455 | 12/1984 | Spendel . |
| 4,832,864 | 5/1989 | Olson . |
| 4,912,056 | 3/1990 | Olson . |
| 5,019,292 | 5/1991 | Baeck et al. . |
| 5,232,851 | 8/1993 | Cox et al. . |

FOREIGN PATENT DOCUMENTS

| | | |
|---|---|---|
| 1 368 599 | 10/1974 | (GB) . |
| 4-352881 | 7/1992 | (JP) . |
| WO 92/07134 | 4/1992 | (WO) . |

*Primary Examiner*—Leon B. Lankford, Jr.
(74) *Attorney, Agent, or Firm*—Burns, Doane Swecker & Mathis LLP

(57) ABSTRACT

Disclosed are strength loss resistant methods for treating cotton toweling with cellulase so as to impart permanent softening to the toweling. In particular, the methods disclosed herein involve the application of a specified amount of cellulase onto one or both of the surfaces of a cotton toweling so as to result in permanent softening of the toweling.

14 Claims, 1 Drawing Sheet

STRENGTH LOSS RESISTANT METHODS FOR IMPROVING THE SOFTENING OF COTTON TOWELING AND RELATED FABRICS

This application is a continuation of application Ser. No. 08/117,648 filed Sep. 8, 1993, now U.S. Pat. No. 6,156,562 which in turn, is a continuation of application Ser. No. 07/810,962 filed Dec. 20, 1991, which is now abandoned.

BACKGROUND OF THE INVENTION

1. Field of the Invention

The present invention is directed to strength loss resistant methods for treating cotton toweling and related fabrics with cellulase so as to impart permanent softening to these fabrics. In particular, the methods of the present invention involve the application of a specified amount of cellulase onto the surface fibers of cotton toweling and related fabrics so as to result in permanent softening of such fabrics. On the other hand, since a specified amount of cellulase is applied only onto the surface fibers of such fabrics, the base fibers (i.e., the interior fibers) of the fabric are not exposed to significant quantities of cellulase. In turn, the interior fibers are not significantly degraded by cellulase and accordingly, strength loss in the treated fabric is reduced as compared to the strength loss arising from treating all of the fibers of the fabric with cellulase.

The methods of the present invention are particularly suitable for use in both a continuous and batch process for treating cotton toweling and related fabrics with cellulase.

2. State of the Art

The use of cellulase to impart permanent softening properties to cotton toweling and related materials is well known in the art. For example, cotton toweling can be treated in a batch or continuous process whereby the treated fabric is washed (immersed) in a cellulase solution at specified conditions. Under such conditions, both the interior and the surface cotton fibers of the fabric are exposed to the cellulase solution. After treatment, the fabric is generally rinsed and dried. Under these conditions, such treatment with cellulase results in permanent softening for the fabric.

However, there is a problem with the treatment of cotton toweling and related fabrics in the manner of the prior art. Specifically, when treated in heretofore known methods for imparting permanent softening, such fabrics experience undesirable weight loss, reduced tensile strength and reduced absorbency. These detrimental attributes can be so severe as to render the treated fabric a poorer quality product as compared to the fabric prior to treatment.

In view of the above, methods for treating cotton toweling and related fabrics which impart permanent softening properties to such fabrics but which also result in reductions in the undesirable properties imparted by prior art processes would be particularly advantageous.

SUMMARY OF THE INVENTION

The present invention is directed to new methods for treating cotton toweling and related fabrics with cellulase so as to impart permanent softening to such fabrics. Unlike prior art processes for imparting permanent softening to such fabrics by exposing the entire fabric to the cellulase solution, the present invention is directed to the discovery that substantial and unexpected improvements are achieved when a specified amount of cellulase is applied onto the surface(s) of cotton toweling and related fabrics ("cotton toweling" as defined herein below). Specifically, the methods of the present invention impart permanent softening to the so treated cotton toweling while also providing for substantial reductions in strength loss, weight loss and loss of absorbency as compared to strength loss, weight loss and loss of absorbency achieved in cotton toweling treated with prior art processes.

Accordingly, in one of its method aspects, the present invention is directed to a method for imparting permanent softening to cotton toweling by treatment with cellulase which method comprises:

(a) applying onto the surface or surfaces of said cotton toweling an aqueous cellulase solution comprising at least about 0.2 grams per liter cellulase wherein the weight amount of said aqueous cellulase solution applied onto the surface(s) of said toweling is between about 10 to 50 percent of the weight of said toweling; and (b) maintaining said toweling under conditions sufficient to impart softening to said toweling.

In a preferred embodiment, the application of the aqueous cellulase solution to the surface or surfaces of the toweling is by way of spraying and even more preferably by a substantially uniform spraying of the aqueous cellulase solution over the surface or surfaces of the toweling.

In another preferred embodiment, the application of the cellulase solution is to both surfaces of the cotton toweling and even more preferably, the application to both surfaces is conducted simultaneously.

After treatment in the process of this invention, the cotton toweling is then treated in a manner to remove and/or inactivate the cellulase enzyme. One method of removing the enzyme is by thoroughly rinsing the so treated toweling with a cellulase free aqueous solution (i.e., an aqueous solution containing no cellulase). In such an embodiment, the toweling is then dried at elevated temperatures to inactivate any enzyme remaining. Alternatively, the toweling is first treated to inactivate the cellulase enzyme by heating to sufficiently high temperatures for a sufficiently long period of time to inactivate the enzyme. In this embodiment, after inactivation, the toweling can subsequently be thoroughly rinsed and dried.

In one of its articles of manufacture aspects, the present invention is directed to cotton toweling which is permanently soft which toweling is prepared by the methods of this invention.

DETAILED DESCRIPTION OF THE PREFERRED EMBODIMENTS

Figure 1A:
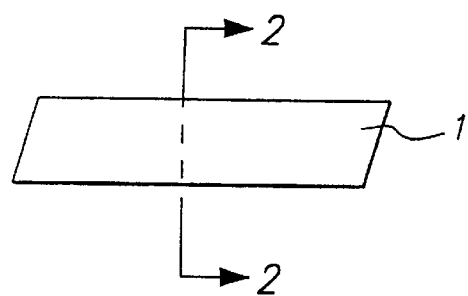
FIG. 1A illustrates a plan view of a cotton toweling useful in the methods of this invention and FIG. 1B illustrates an enlarged cross-sectional view of this fabric taken along lines, 2—2.

As noted above, the present invention is directed to methods for treating cotton toweling with cellulase so as to impart permanent softening to the toweling which methods involve applying an aqueous cellulase solution to the surface of the toweling. However, prior to discussing this invention in further detail, the following terms will first be defined:

1. Definitions.

As used herein, the following terms have the meanings given below:

The term "toweling" refers to toweling as well as to related materials having a similar construction as toweling. In this regard, it is art recognized that toweling is constructed by forming one or more loops which extend both above and/or below a plane of base fibers. Accordingly, related materials include, for example, velour, corduroy, and the like, which possess similar construction to toweling with the exception that some or all of the loops are clipped (broken).

The term "cotton toweling" refers to toweling made of 100% cotton or cotton blends. When cotton blends are employed, the amount of cotton in such toweling should be at least about 40 percent by weight percent cotton; preferably, more than about 60 percent by weight cotton; and most preferably, more than about 75 percent by weight cotton. When employed as blends, the companion material employed in the fabric can include one or more non-cotton fibers including synthetic fibers such as polyamide fibers (for example, nylon 6 and nylon 66), acrylic fibers (for example, polyacrylonitrile fibers), polyester fibers (for example, polyethylene terephthalate), polyvinyl alcohol fibers (for example, Vinylon), polyvinyl chloride fibers, polyvinylidene chloride fibers, polyurethane fibers, polyurea fibers and aramid fibers. It is contemplated that regenerated cellulose, such as rayon, could be used as a substitute for cotton in cotton toweling.

The term "finishing" as employed herein means the application of a sufficient amount of finish to the cotton toweling so as to substantially prevent cellulolytic activity of the cellulase on the toweling. Finishes are generally applied at or near the end of the manufacturing process of the toweling for the purpose of enhancing the properties of the toweling, for example, softness, drapability, etc., which additionally protects the toweling from reaction with cellulases. Finishes useful for finishing cotton toweling are well known in the art and include, for example quatenary salts and other softners.

The term "cellulose" as employed herein refers to an enzyme composition derived from a microorganism which acts on crystalline forms of cellulose and its derivatives to hydrolyze cellulose and give primary products, glucose and cellobiose. Such cellulases are synthesized by a large number of microorganisms including fungi, actinomycetes, gliding bacteria (mycobacteria) and true bacteria. Some microorganisms capable of producing cellulases useful in the methods disclosed herein are disclosed in British Patent No. 2 094 826A, the disclosure of which is incorporated herein by reference. Most cellulases generally have their optimum activity in the acidic or neutral pH range. On the other hand, alkaline cellulases, i.e., cellulases showing optimum activity in neutral or alkaline media, are also known in the art. Microorganisms producing alkaline cellulases are disclosed in U.S. Pat. No. 4,822,516, the disclosure of which is incorporated herein by reference. Other references disclosing alkaline cellulases are EPA Publication No. 269,977 and EPA Publication No. 265,832, the disclosures of which are also incorporated herein by reference.

Cellulase produced by a naturally occurring microorganism is sometimes referred to herein as a "cellulose system" to distinguish it from the classifications and classification components isolated therefrom. Such classifications are well known in the art and include exo-cellobiohydrolases ("CBH"), endoglucanases ("EG") and β-glucosidases ("BG"). Additionally, there are multiple components in each classification. For example, in the cellulase obtained from *Trichoderma reesei*, there are two CBH components, i.e., CBH I and CBH II, and at least three EG components, EG I, EG II and EG III.

The different classifications are known in the art to synergistically interact with each other to provide enhanced activity against cellulose. Thus, while a cellulase system derived from any microorganism can be employed herein, it may be preferable that the cellulase system contain at least one CBH component and at least one EG component so that enhanced cellulase activity is achieved.

The fermentation procedures for culturing cellulolytic microorganisms for production of cellulase are known per se in the art. For example, cellulase systems can be produced either by solid or submerged culture, including batch, fed-batch and continuous-flow processes. The collection and purification of the cellulase systems from the fermentation broth can also be effected by procedures known per se in the art.

Preferred cellulases for use in this invention are those obtained from *Trichoderma reesei*, *T. koningii*, Pencillum sp., *Humicola insolens*, and the like. Certain cellulases are commercially available, i.e., CELLUCLAST (available from Novo Industry, Copenhagen, Denmark), RAPIDASE (available from Gist Brocades, N.V., Delft, Holland), CYTOLASE 123 (available from Genencor International, South San Francisco, Calif.) and the like. Other cellulases can be readily isolated by art recognized fermentation and isolation procedures.

The term "surface active agent or surfactant" refers to anionic, non-ionic and ampholytic surfactants well known in the art.

The term "buffer" refers to art recognized acid/base reagents which stabilize the cellulase solution against undesired pH shifts during the cellulase treatment of the cotton-containing fabric.

The term "aqueous cellulase solution" means an aqueous solution containing cellulase and optional additives such as surfactants, buffers, and the like. In general, the aqueous cellulase solution will contain at least about 0.2 grams of cellulase per liter and, preferably, from about 0.4 grams of cellulase to about 1.0 grams of cellulase per liter of solution. In this application, all references to grams of cellulase per liter refer to grams of cellulase protein (CBH, EG and BG components) with non-cellulase components being excluded.

Surprisingly, it has been found that it is the amount of cellulase protein and not its relative rate of hydrolysis of crystalline cellulose to glucose which provides for the improvements cited herein.

In order to improve the wettability of the solution, the aqueous cellulase solution may contain from about 0.1 to about 5 weight percent of a surfactant and preferably from about 0.2 to 2 weight percent of surfactant based on the total weight of the aqueous cellulase solution.

The aqueous cellulase solution is generally maintained at a pH where the cellulase possesses significant cellulolytic activity. In this regard, it is art recognized that cellulase activity is pH dependent. That is to say that a specific cellulase composition will exhibit significant cellulolytic activity within a defined pH range with optimal cellulolytic activity generally being found within a small portion of this defined range. The specific pH range for cellulolytic activity will vary with each cellulase composition. As noted above, while most cellulases will exhibit cellulolytic activity within an acidic to neutral pH profile, there are some cellulase compositions which exhibit cellulolytic activity in an alkaline pH profile.

During treatment of cotton toweling, it is possible that the pH of the initial cellulase solution could be outside the range required for significant cellulase activity. It is further possible for the pH to change during treatment of the cotton toweling, for example, by the generation of reaction product(s) which alters the pH of the solution. In either event, the pH of an unbuffered cellulase solution could be outside the range required for significant cellulolytic activity. When this occurs, undesired reduction or cessation of cellulolytic activity in the cellulase solution occurs. For example, if a cellulase having an acidic activity profile is employed in a neutral or alkaline unbuffered aqueous solution, then the pH of the solution will result in lower cellulolytic activity and possibly in the cessation of cellulolytic activity. On the other hand, the use of a cellulase having a neutral or alkaline pH profile in a neutral unbuffered aqueous solution should initially provide significant cellulolytic activity.

In view of the above, the pH of the cellulase solution should be maintained within the range required for significant cellulolytic activity. One means of accomplishing this is by simply adjusting the pH as required by the addition of either an acid or a base. However, in a preferred embodiment, the pH of the system is preferably maintained within the desired pH range by the use of a buffer in the cellulase solution. In general, a sufficient amount of buffer is employed so as to maintain the pH of the solution within the range wherein the employed cellulase exhibits activity and preferably where the cellulase exhibits optimal activity. Insofar as different cellulase compositions have different pH ranges for exhibiting cellulase activity, the specific buffer employed is selected in relationship to the specific cellulase composition employed. The buffer(s) selected for use with the cellulase composition employed can be readily determined by the skilled artisan taking into account the pH range and optimum for the cellulase composition employed as well as the pH of the cellulase solution. Preferably, the buffer employed is one which is compatible with the cellulase composition and which will maintain the pH of the cellulase solution within the pH range required for optimal activity. Suitable buffers include sodium citrate, ammonium acetate, sodium acetate, disodium phosphate, and any other art recognized buffers. In general, such buffers are employed in concentrations of at least 0.005 N and greater. Preferably, the concentration of the buffer in the cellulase solution is from about 0.01 to about 0.5 N, and more preferably, from about 0.05 to about 0.15 N. In general, increased buffer concentrations in the cellulase solution may cause enhanced rates of tensile strength loss of the treated cotton toweling.

The tensile strength of cotton toweling can be measured in a warp and filling direction which are at right angles to each other. Accordingly, the term "warp tensile strength" as used herein refers to the tensile strength of the cotton toweling as measured along its length whereas the term "filling tensile strength" refers to the tensile strength of the cotton toweling as measured across its width.

The tensile strength of cotton toweling is readily conducted following ASTM D1682 test methodology. Equipment suitable for testing the tensile strength of such fabrics include a Scott tester or an Instron tester, both of which are commercially available. In testing the tensile strength of cotton toweling which has been treated with a cellulase solution in the manner of this invention, care should be taken to prevent fabric shrinkage after treatment and before testing. Such shrinkage would result in erroneous tensile strength data.

2. Methodology

In the methods of the present invention, the aqueous cellulase solution is applied onto the surface or surfaces of the cotton toweling in either a continuous or batch process. Methods for applying the cellulase solution to the surface of the cotton toweling include, by way of example, painting the solution onto the surface of the toweling, spraying the solution onto the surface of the cloth, and the like. In either case, while some of the cellulase solution may penetrate into the interior fibers of the toweling, a substantial portion of the cellulase solution will remain on the surface of the toweling.

In a preferred embodiment, the aqueous cellulase solution is applied to one or both surfaces of the toweling and preferably, the methods of this invention are conducted prior to the application of any finish to the toweling.

Sufficient amounts of the aqueous cellulase solution are applied onto the surface(s) of the toweling so that the weight amount of the solution applied onto the toweling is between about 10 to 50 percent of the weight of the toweling (before treatment and weighed dry) and, preferably between about 30 to 50 percent of the weight of the toweling. In particular, if the weight amount of solution employed is greater than 50% of the weight of the toweling to be treated, strength loss will be too great. Likewise, if the weight amount of the solution employed is less than about 10% of the weight of the toweling to be treated, then the cellulase will not impart the desired softening.

After application of the aqueous cellulase solution, the toweling is generally maintained under conditions sufficient to impart permanent softening to the toweling. Preferably, this includes maintaining the toweling at an elevated temperature, i.e., about 20° C. to about 65° C. and preferably about 35° C. to about 60° C., for a period of time from about 1 to about 16 hours.

In another preferred embodiment, the toweling is maintained in an environment which does not permit substantial dehydration thereto. Under these conditions, permanent softening is imparted to the toweling.

Figure 1B:

Without being limited to any theory, it is believed that the application of the aqueous cellulase solution to the surface(s) of cotton toweling exposes the cellulose in the fiber loops of the toweling to cellulase while minimizing exposure of the interior fibers, i.e., the base fabric, to cellulase. In this regard, FIG. 1A illustrates a plan view of a cotton toweling, 1, and FIG. 1B illustrates an enlarged cross-sectional view of cotton toweling, 1, taken along lines, 2—2. In FIG. 1B, fiber loops, 3, are found on the surface of toweling, 1, whereas, the remainder of the fiber is in the interior of toweling, 1. Since the fiber loops, 3, are generally on the surface of toweling, 1, applying the aqueous cellulase solution to the surface of the cotton toweling, 1, exposes these fiber loops to cellulase without exposing the interior fibers to cellulase.

Again, without being limited to any theory, it is further believed that the action of the cellulase on the fiber loops results in some breakdown of the crystalline portion of cellulose in these loops which breakdown reduces the stiffness of the loop. Reduction in the stiffness of the loop results in permanent softening to the toweling which is achieved without the need to treat all of the cotton fibers in the toweling.

After maintaining the cotton toweling under conditions sufficient to impart permanent softening to the toweling, the toweling is then treated in a manner to remove and/or inactivate the cellulase enzyme. One method of removing the enzyme is to thoroughly rinse the toweling with a cellulase free aqueous solution. In such an embodiment, the toweling is then dried at elevated temperatures (e.g., at a temperature of at least about 75° C.) to inactivate any enzyme remaining after rinsing. Alternatively, the treated toweling can be first after-treated to inactivate the cellulase enzyme by heating to sufficiently high temperatures for a sufficiently long period of time to inactivate the enzyme (e.g., at a temperature of at least about 75° C. for a period of at least 10 minutes). In this embodiment, the toweling is then usually thoroughly rinsed and dried.

The methods of this invention are suitable for either a batch process or a continuous process. For example, in production, a preferred application of aqueous cellulase solution onto the surface(s) of cotton toweling can be carried out in a continuous manner and the treated toweling can be moved into a J-Box where the toweling will be maintained under conditions sufficient to impart permanent softening, e.g., 1–3 hours at about 50° to about 60° C. The toweling can then be passed through a continuous rope washer containing a dilute cellulase solution (i.e., about 0.1 grams/liter to about 0.25 grams/liter at from about 50° C. to about 60° C.) and then thoroughly rinsed and dried. When a rope washer is employed, it preferably contains a minimum of 4 bowls, and more preferably 7 bowls to ensure complete enzymatic action on the cellulose which provides softening to the base fabric without unsatisfactory strength loss.

Alternatively, in a preferred batch process, after application of the aqueous cellulase solution to the surface(s) of cotton toweling, the toweling can be rolled up, covered with plastic, and maintained under conditions sufficient to impart permanent softening, i.e., about 30° to about 60° C. for about 1 to 8 hours. Afterwards, the toweling can then be passed through a continuous rope washer containing a dilute cellulase solution (i.e., about 0.05 grams/liter to about 0.5 grams/liter at from about 50° C. to about 60° C.) and then thoroughly rinsed with a cellulase free aqueous solution and then dried.

The use of a dilute cellulase solution in the continuous rope washer provides for removal of loose fibers. However, the conditions are such that there is a minimal effect on additional strength loss in the toweling.

Figure 2:
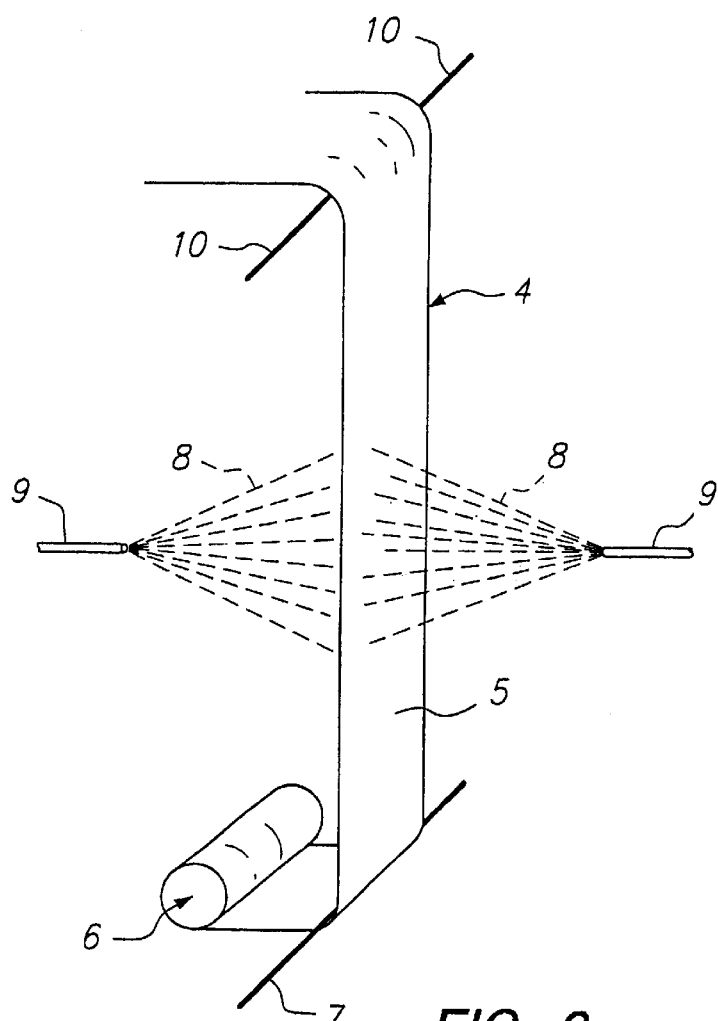
FIG. 2 illustrates continuous and simultaneous application of an aqueous cellulase solution to both surfaces of cotton toweling.

FIG. 2 illustrates one means of continuously and simultaneously applying an aqueous cellulase solution onto both surfaces of cotton toweling. In FIG. 2, apparatus, 4, comprises a cotton toweling, 5, which is stored at roller, 6, prior to application of the aqueous cellulase solution. The direction of that part of the toweling departing roller, 6, is changed by guide member, 7, so that the toweling is moving in a vertical direction. While moving in a vertical direction, a requisite amount of the aqueous cellulase solution is applied onto the surfaces of toweling, 5, via sprays, 8, which are generated from feedlines, 9. Feedlines, 9, are connected to a tank (not shown) containing a reservoir of the aqueous cellulase solution. If necessary, additional sprays, 6, can be generated so as to cover more surface area or to provide a substantially uniform application of cellulase solution over the surfaces of the cotton toweling, 5. In general, application of the cellulase solution onto the cotton toweling, 5, is considered substantially uniform if the variation in application rate is no more than about ±2%.

After application of the aqueous cellulase solution, the direction of toweling, 5, is changed by guide member, 10. Toweling, 5, can then be moved to another roller (not shown) for batch treatment of the toweling under conditions sufficient to impart permanent softening; or toweling, 5, can be moved to a J-box for continuous treatment of toweling, 5, under conditions sufficient to impart permanent softening. In either case, after the toweling has completed treatment, it is generally sized (cut) into dimensions suitable for use as consumer goods.

The following examples are offered to illustrate the present invention and should not be construed in any way as limiting its scope.

In these examples, the following abbreviations have the following meanings:

° C. = degree Centigrade
° F. = degree Fahrenheit
g = gram
l = liter
lbs = pounds
oz. = ounces

EXAMPLES

Comparative Example A

Cotton toweling (made from 100% cotton terry cloth) was treated with cellulase in a prior art batch method to impart permanent softening. Specifically, samples of the same toweling were washed in different aqueous cellulase solutions obtained by adding either about 0.4 g/l or about 0.8 g/l of cellulase protein (from Primafast™ 100 cellulase, derived from *Trichoderma reesei* and which is available from Gresco Mfg. Co., Thomasville, N.C., 27360) to water. The aqueous solution was buffered at pH 4.5 to 5.0 by the addition of 3.6 g/l of acetic acid (56%) and 1.9 g/l of caustic (50%). The toweling was washed for 45 minutes at 57° C. (135° F.), rinsed, and then dried.

Toweling treated with cellulase possessed improved softening; however, its physical properties were adversely affected as shown in Table I below:

TABLE I

|  | Standard | TOWEL 0.8 g/l Cellulase | 0.4 g/l Cellulase |
|---|---|---|---|
| Total Weight (oz) | 16.22 | 11.92 | 11.22 |
| Tensile Strength (lbs) | | | |
| Warp Direction | 75 | 41 | 43 |
| Filling Direction | 78 | 35 | 38 |
| Absorbency*: | 242 | 68 | 180 |

*Absorbency is measured in arbitrary units and higher absorbency values reflect more absorbent toweling The above data demonstrates that prior art methods for treating cotton toweling result in substantial reductions in weight, tensile strength (in both the warp and filling direction) and in absorbency.

Example 1

Cotton toweling (made from 100% cotton terry cloth) was treated with cellulase in the manner of this invention to impart permanent softening. Specifically, the toweling was sprayed on both sides (25% wet add-on to each side) with the following cellulase formulation:

0.4 g/l Cellulase Protein (from Primafast™ 100 Cellulase)
1.9 g/l Caustic, 50%
3.6 g/l Acetic Acid, 56%
0.5 g/l Nonionic Surfactant (wetting agent)

After spraying, the toweling was rolled up and secured in plastic to prevent moisture evaporation. The toweling was then batched for 2 hours at 135° F. (56° C.); then removed and held in the washing machine containing 90 liters of the cellulase solution described above with the exception that the cellulose enzyme concentration was 0.2 g/l. The toweling was then washed at 135° F. (56° C.) for 30 minutes, rinsed and tumbled dried.

The so treated toweling possessed permanent softening and had the following physical properties:

|  | TOWEL | |
| --- | --- | --- |
|  | Standard | Example 1 |
| Total Weight (oz) | 16.22 | 13.54 |
| Tensile Strength (lbs) | | |
| Warp Direction | 75 | 60 |
| Fill Direction | 78 | 62 |
| Absorbency*: | 150 minimum | 235 |

*Absorbency is measured in arbitrary units and higher absorbency values reflect more absorbent toweling Example 2

An aqueous cellulase solution is applied to a cotton-containing towel (100% cotton terry cloth) in the manner of Example 1 above. After batching the towel in a J-box for 1–3 hours at 57° C., the towel is passed through a continuous washing step employing a rope washer having 7 bowls. The first six bowls can contain the following solution:

0.2–1 g/l Cellulase Protein (from Primafast™ 100)
3.6 g/l Acetic acid, 56%
1.9 g/l Sodium Hydroxide, 50%
0.25–1.0 g/l Surfactant (optional)

Each of the first six bowls generally contains the same solution whereas the 7th bowl can be used to deactivate the cellulase by utilizing an aqueous solution maintained at a temperature of 180–200° F. (82° to 93° C.). The cellulase can also be inactivated if the treated goods go directly into a dryer after the continuous washing range. The time of treatment in the continuous range should be 20–60 minutes. The speed of the fabric through the range will be controlled by the treatment minutes required to achieve the desired softness.

Similarly, by following the procedures set forth in Examples 1 and 2 above, other cellulases, including cellulase derived from microorganisms other than *Trichoderma reesei*, could be employed merely by substituting for Primafast™ 100 cellulase. Other suitable cellulases which are commercially available and which could be employed herein include CELLUCAST, RAPIDASE, and the like. Likewise, the application of the aqueous cellulase solution to the surfaces of the cotton toweling can be achieved by any other art recognized methods including painting the solution onto the surface(s) of the toweling and the like.

What is claimed is:

1. A permanently soft cotton toweling manufactured by treatment with cellulase prepared by the method comprising:
   (a) applying onto the surfaces of said toweling prior to application of a finish to said toweling an aqueous cellulase solution containing at least about 0.2 grams per liter cellulase wherein the weight amount of said aqueous cellulase solution applied onto the surface(s) of said toweling is between about 10 to 50 percent of the weight of said toweling and further wherein said aqueous cellulase solution is free of surfactant;
   (b) incubating the toweling at a temperature of from about 20° to about 65° C. for a period of from about 1 to about 16 hours to impart softening and/or inactivate the cellulase enzyme;
   (c) treating the cotton toweling in a manner to remove and/or inactivate the cellulase enzyme;
   wherein said cotton toweling after treatment when compared to standard cotton toweling is characterized by retaining at least: 83.47% of the total weight, 80% of the tensile strength in the warp direction, and 79.48% of the tensile strength in the fill direction.

2. The permanently soft cotton toweling according to claim 1, wherein the application of said aqueous cellulase solution to said toweling is by spraying and further wherein after incubation step (b) and prior to treating step (c) the cotton toweling is washed in a continuous washer containing a dilute aqueous cellulase solution which in the case where the toweling is produced from a continuous process contains from about 0.1 to 0.25 grams of cellulase per liter of solution and in the case where the toweling is produced from a batch process contains from about 0.05 to 0.5 grams of cellulase per liter of solution wherein the washing is conducted under conditions to remove loose fibers from the cotton toweling.

3. The permanently soft cotton toweling according to claim 2 wherein the spraying of the aqueous cellulase solution is over both surfaces of the toweling.

4. The permanently soft cotton toweling according to claim 3 wherein both surfaces of said toweling are sprayed simultaneously.

5. The permanently soft cotton toweling according to claim 1 wherein said cellulase enzyme is removed by washing the toweling with a cellulase free aqueous solution.

6. The permanently soft cotton toweling according to claim 5 wherein after removal of said enzyme, the toweling is dried at a temperature sufficiently high to both dry the toweling and to inactivate any remaining cellulase enzyme.

7. The permanently soft cotton toweling according to claim 1 wherein said cellulase enzyme is inactivated by heating the toweling at a temperature and time sufficient to inactivate said enzyme.

8. The permanently soft cotton toweling according to claim 7 wherein said cellulase enzyme is inactivated by heating the cellulase containing cotton toweling to a temperature of at least 75° C. for at least 10 minutes.

9. The permanently soft cotton toweling according to claim 7 wherein after inactivation of said enzyme, the toweling is washed with a cellulase free aqueous solution and then dried.

10. The permanently soft cotton toweling according to claim 1 wherein said aqueous cellulase solution additionally contains a compatible buffer at a concentration of at least 0.005 N.

11. The permanently soft cotton toweling according to claim 1 wherein said cellulase enzyme is derived from a fungal microorganism.

12. The permanently soft cotton toweling according to claim 11 wherein said fungal microorganism is selected from the group consisting of *Trichoderma reesei*, *Trichoderma koningii*, Pencillum sp., and *Humicola isolens*.

13. The permanently soft cotton toweling according to claim 1 wherein said aqueous cellulase solution contains from about 0.2 to about 1 gram per liter of cellulase.

14. The permanently soft cotton toweling according to claim 13 wherein said aqueous cellulase solution contains about 0.4 grams per liter of cellulase.

* * * * *